«12» United States Patent
Bruder et al.

(10) Patent No.: US 7,486,762 B2
(45) Date of Patent: Feb. 3, 2009

(54) PRODUCTION OF CT IMAGES BY SPIRAL RECONSTRUCTION OF AN OBJECT FOR EXAMINATION MOVING IN A PARTIALLY CYCLICAL MANNER

(75) Inventors: Herbert Bruder, Höchstadt (DE); Thomas Flohr, Uehlfeld (DE); Matthias Niethammer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/556,943

(22) PCT Filed: Apr. 23, 2004

(86) PCT No.: PCT/EP2004/004348

§ 371 (c)(1),
(2), (4) Date: Nov. 2, 2006

(87) PCT Pub. No.: WO2004/100791

PCT Pub. Date: Nov. 25, 2004

(65) Prior Publication Data

US 2007/0092057 A1 Apr. 26, 2007

(30) Foreign Application Priority Data

May 16, 2003 (DE) .................... 103 22 139

(51) Int. Cl.
*G01N 23/00* (2006.01)
(52) U.S. Cl. ............................ 378/15; 378/8
(58) Field of Classification Search ............... 378/4–20, 378/8, 901
See application file for complete search history.

(56) References Cited

U.S. PATENT DOCUMENTS 5,046,003 A * 9/1991 Crawford ................. 378/15

(Continued)

FOREIGN PATENT DOCUMENTS

| DE | 197 42 119 A1 | 9/1997 |
| DE | 198 42 238 A1 | 9/1998 |
| DE | 100 64 785 A1 | 12/2000 |
| EP | 1 340 460 A1 | 2/2003 |

OTHER PUBLICATIONS

Röntgen-Computertomographie, (Heinz Morneburg), Seiten 429 bis 435 Bildgebende Systeme der medizinsichen Diagnostik.
Spiral-CT (Willi A. Kalender), Seiten 65 bis 74, Computer-Tomographie.
International Search Report, Written Opinion and English translation thereof, German OA issued Feb. 20, 2004, and German translation Aid.

*Primary Examiner*—Edward J Glick
*Assistant Examiner*—Alexander H Taningco
(74) *Attorney, Agent, or Firm*—Harness, Dickey & Pierce, P.L.C.

(57) ABSTRACT

A method is disclosed for the production of CT images via a CT spiral reconstruction of object for examination moving in partial areas in a cyclical manner and a CT device therefor. During scanning of the object to be examined, various rates of advancement are used, irrespective of whether the scanned area is at least partially cyclically displaced or is stationary.

15 Claims, 3 Drawing Sheets

U.S. PATENT DOCUMENTS

| | | |
|---|---|---|
| 5,539,796 A | 7/1996 | Takagi et al. |
| 5,805,659 A * | 9/1998 | Tam .......................... 378/15 |
| 6,023,494 A * | 2/2000 | Senzig et al. ................. 378/4 |
| 6,185,271 B1 * | 2/2001 | Kinsinger ................... 378/19 |
| 6,421,552 B1 * | 7/2002 | Hsieh ........................ 600/425 |
| 6,556,697 B1 | 4/2003 | Bruder et al. |
| 2003/0092983 A1 * | 5/2003 | Baker et al. ................ 600/428 |
| 2003/0163039 A1 * | 8/2003 | Pan et al. .................... 600/425 |

* cited by examiner

I   II

PRODUCTION OF CT IMAGES BY SPIRAL RECONSTRUCTION OF AN OBJECT FOR EXAMINATION MOVING IN A PARTIALLY CYCLICAL MANNER

This application is the national phase under 35 U.S.C. § 371 of PCT International Application No. PCT/EP2004/004348 which has an International filing date of Apr. 23, 2004, which designated the United States of America and which claims priority on German Patent Application number DE 103 22 139.5 filed May 16, 2003, the entire contents of which are hereby incorporated herein by reference.

FIELD

The invention generally relates to a method and a computed tomography unit (CT unit) for producing CT images by spiral reconstruction of a partially cyclically moving examination object. The examination object can be, for example, a patient. In one example of the method in which in one pass the examination object is scanned by a spiral movement of at least one focus and at least one detector situated opposite, the scanning of the examination region may be performed at a relative feed rate between gantry and couch. Further, a three-dimensional image of the absorption coefficients may be determined with the aid of a multiplicity of sectional planes of an examination volume on the basis of the data obtained by scanning.

BACKGROUND

A method and a CT unit are known, for example, from laid-open patent application DE 198 42 238 A2. This document discloses a recording method for a periodically moving object, in particular a patient's beating heart, having a moving phase and a rest phase via a CT unit having a gantry, rotating spirally around the examination object, with a focus and a multirow detector, the feed rate of the patient couch and the rotational speed of the gantry being tuned to one another for a complete pass or scan in such a way that it is possible to collect sufficient image information for the best possible reconstruction during the rest phase of the periodically moving object. The movement and rest phases can be determined by a connected ECG. No provision is made to change the feed rate during the scan.

A disadvantage with this is a need for a relatively low feed rate that thereby also necessitates accepting a high dose commitment during recording.

Reference is also made to patent U.S. Pat. No. 5,046,003, which describes a method of sequential scanning in which individual image planes are scanned by a single-row detector by moving at the lowest possible feed rate in the local region of these image planes, whereas the feed rate is raised with increasing distance from the nearest image plane. This results in a virtually sinusoidal characteristic of the feed rate over the entire scanning path independently of the movement situation in the scanned area. It appears to be a problem here that the feed rate changing cyclically and in short intervals transfers onto the patient as a whole an uncontrolled movement that leads to fuzziness in the CT recordings.

Also generally known—for example from "Bildgebende Systeme der medizinischen Diagnostik" ["Imaging Systems in Medical Diagnostics"], ISBN 89578-002-2, or "Computer-Tomographie" ["Computer tomography"], ISBN 3-89578-082-0, —on the other hand are the most multifarious CT recording methods, including special reconstruction methods of resting objects, a constant feed rate being used in each case for a complete pass of a scan.

A disadvantage of such methods resides in the poor recording quality as a result of the movement fuzziness in the area of the respectively moving part of the object to be recorded, for example the heart in the case of a patient.

If the aim now is to carry out a CT scan of a patient's lung, the movement of the beating heart leads to instances of movement fuzziness in the area of fine vessels. This movement fuzziness also produces unsatisfactory recording results when differential images are produced from native and contrastive measurements in order to determine the lung perfusion. The two measurements lie apart by approximately 10 seconds, and so they can be carried out with fast CT units during a breath-holding cycle. Nevertheless, the heart movement leads to an interim change in position of the lung and to a displacement between native and contrastive image. Were the recording to be carried out, alternatively, in accordance with the method of a cardio CT, on the one hand the recording period would be too long such that a breath-holding cycle would be insufficient for the two recordings, and on the other hand the applied dose would be too high for the patient.

SUMMARY

It is an object of at least one embodiment of the invention to find a method for producing CT images of an at least partially cyclically moving examination object, and a CT unit for carrying out this method, that on the one hand enables cyclically moving areas to be displayed with intense sharpness, and on the other hand keeps the recording time for the overall examination object as short as possible.

The inventors have realized that this object can be achieved by using different feed rates during a scanning pass, depending on whether precisely an area with strong changes of movement or a largely static area is being scanned. It is thereby possible when scanning the moving area to use a reconstruction method known per se from cardio CT with a relatively low feed rate, and when scanning largely static areas to use the normal reconstruction method with a high feed rate.

When scanning the moving area, it is preferred for the purpose of image reconstruction to use only data that originate from a rest phase of the cyclical movement, whereas data from the movement phase are not processed. In order to compensate the scanning periods that cannot be used, it is thereby necessary to employ a lower feed rate, whereas a substantially higher feed rate can be used during scanning of a static object area without the need to accept losses in the completeness of the scanning. The overall result is thus a short overall scanning time such that one native and one contrastive 3D recording each can be made for producing a 3D differential image even during a single breath-holding cycle.

In the sense of at least one embodiment of the invention, feed rate is to be understood as the relative speed between the CT unit and the examination object, mostly a patient located on a movable couch. Furthermore, the cyclical movement does not relate to the movement of the overall examination object, but the cyclical movement of a subarea relative to the entire examination object such as, for example, the movement of the heart and, if appropriate, surrounding areas because of the intrinsic heart movement.

On the basis of this fundamental idea, the inventors now propose to improve the known method for producing CT images of a partially cyclically moving examination object, preferably of a patient. In one pass the examination object is scanned by a spiral movement of at least one focus and at least one detector situated opposite, the scanning of the examination region is performed at a relative feed rate $v_t$ between gantry and couch, and a three-dimensional image of the absorption coefficients is determined with the aid of a multiplicity of sectional planes of an examination volume on the basis of the data obtained by scanning.

According to at least one embodiment of the invention, at least one static object area and at least one moving object area are determined with reference to the examination object (P) with the aid of cyclical intrinsic movement. Further, during a pass when scanning the examination object (P) a first feed rate $(v_1)$ is used in the at least one moving object area, and another, second feed rate $(v_2)$ is used in the at least one static object area.

Fundamentally two different variants of this method are possible by which different feed rates can be used for operating during a scanning pass.

On the one hand, the examination object can be subdivided before the scan into moving and nonmoving areas such that the feed rate is matched during the pass in accordance with the respectively scanned area. In this process, a high feed rate is selected for the nonmoving or static subareas of the examination object, and a low feed rate is selected in the moving area. It is then possible in the case of the low feed rate to use the methods known per se for recording cyclically moving objects, preferably with rest phases and movement phases.

On the other hand, during the pass it can be detected by evaluation of the scanning itself whether a movement is present in the current scanning area or not. It is thus determined during the scan whether the currently scanned area is a moving subarea or a static subarea of the object, and the feed rate is regulated on line, as it were, as a function of the movement situation of the scanned area. Thus, by contrast with the first variant, which requires a preview in order to determine the differently treated subareas, a switchover is made automatically or semiautomatically during the scanning pass between a normal CT scan, in which all determined detector data are used for reconstruction, and a cardio CT scan, in which only detector data from specific phase segments of a cyclical movement are used for reconstruction. For example, in the case of the semiautomatic switchover the operating staff can be advised of the required change in speed by an appropriate signal, and undertake this change manually.

For example, in the case of both variants it is possible to make use in static areas of a reconstruction method such as is described in the laid-open patent application DE 101 27 269 A1, and to switch over to the appropriate cardio method in accordance with the laid-open patent application DE 102 07 623 A1 upon transition to the area with cyclical movement. However, it may be expressly pointed out that the method according to at least one embodiment of the invention is not limited to-these reconstruction methods specified here, but can be used with all known spiral reconstruction methods.

In accordance with the first outlined variant of the method, the inventors propose that a higher feed rate $v_2$ serves for scanning a static object area, and a lower feed rate $v_1$ serves for scanning a moving object area.

For example, the position of the beating heart can be determined in order to divide the examination object into static and moving object areas, it also being possible for predetermined border areas that are likewise excited to movements by the beating heart likewise to be incorporated in the area that is moving by definition.

Such a determination of static and moving object areas before the scan can be performed, for example, by at least one topogram recording, sometimes also called a scout scan.

In this way, the examination object is moved in a longitudinal direction relative to the gantry with nonrotating focus and detector, and an X-ray recording is obtained.

Alternatively, the determination of static and moving object areas before the scan can also be performed by at least one optical recording.

A particularly advantageous refinement of the method according to at least one embodiment of the invention provides that the transition between the feed rates is performed with a prescribed maximum acceleration. This prevents the examination object, particularly when it is a patient, from being excited by the process to strong acceleration, in particular to movements that have a disturbing effect. If such an influence on the patient is to be completely avoided, it is possible to use a movable gantry with patients stationary in space, as against the otherwise customary design of CT units for the relative movement of gantry and patient. In such a case, the patient or the examination object is not influenced by the variation in the feed rates.

The inventors also propose that the determination of moving and static object areas is performed during the scan, and a low feed rate $(v_1)$ is selected upon detection of a cyclical movement, and a higher feed rate $(v_2)$ is selected upon detection of a static state.

In this particular design of at least one embodiment of the method, it is provided that the detection of the movement of the examination object is performed in the current scanning area and preferably during the scan by virtue of the fact that the intensity measurement of at least one pair of rays on a common ray axis, preferably of two oppositely directed rays, is compared to two consecutive instants. Use is made here of the circumstance that in the case of multirow spiral CT the total absorption of the same beam path by the examination object is measured multiply in a fashion offset in time, and it is possible to infer a variation—that is to say a movement—within the beam path on the basis of changes in the absorption measurement. Reference is made by way of example to laid-open patent application DE 100 64 785 A1 (priority application from U.S. Pat. No. 472,560) with reference to this basically known method of detecting moving and unmoving areas.

Furthermore, in a special design of the method during scanning at a low feed rate the movement of the heart can temporally be resolved by use of ECG leads and divided into movement phases and rest phases, only detected data from the rest phase being used to compile images. With such a "gated" recording method, preferably a cardio recording method, instead of using the ECG signal as signal for determining cyclical phases, in particular rest and movement phases, it is also possible to use movement information from imaging projection data of the CT that are offset by 180°, and to generate therefrom a trigger signal for a movement-gated recording method of the moving area.

Use can be made when scanning the moving area of a CT spiral reconstruction method that uses only detector data from a specific cyclical phase of the cyclically moving area, whereas during scanning of the static area use is made of a spiral reconstruction method that uses all the measured detector data for the reconstruction.

For the purpose of noise-equivalent display in the static and moving examination areas, it is also proposed that the intensity of radiation emanating from the at least one focus is matched to the respectively current feed rate $v_r$. This can be performed, for example, by controlling/regulating the tube current in the X-ray tubes.

In addition to the method according to at least one embodiment of the invention, the inventors also propose to improve a CT unit that serves for scanning an at least partially cyclically moving examination object, preferably a patient, and is equipped with a beam emanating from at least one focus, and having at least one detector array of planar design and with a multiplicity of distributed detector elements for detecting the rays of the beam, the at least one focus being moved relative to the examination object with a feed rate $v_t$ on a spiral focal track revolving about the examination object. The improvement resides in that at least steps/devices/apparatuses for carrying out the method outlined above are included, where the steps/devices/apparatuses can be implemented at least partially by programs or program modules.

In a corresponding way, the CT unit according to at least one embodiment of the invention can have an apparatus that is provided for controlling the feed rate $v_t$ as a function of movement status and/or scanning area.

BRIEF DESCRIPTION OF THE DRAWINGS

The invention is explained below in more detail with the aid of the example embodiments illustrated in the attached schematics, the following abbreviations being used in the FIGS.—1: focus; 2: detector; 3: X-ray beam; 4: data processing system; 5: output unit; 6: input unit; G: border area of movement; H: heart; L: couch; M: central axis of the spiral track; P: patient/examination object; S: spiral track of the focus; T: topogram; t: time; $v_t$: feed rate; $v_1$: low feed rate; $v_2$: high feed rate; V: feed; x: x-axis; z: z-axis; α: stationary area; β: area with movement; γ: intermediate area of movement area in relation to stationary area.

The figures show the following.

DETAILED DESCRIPTION OF THE EXAMPLE EMBODIMENTS

Figure 1:
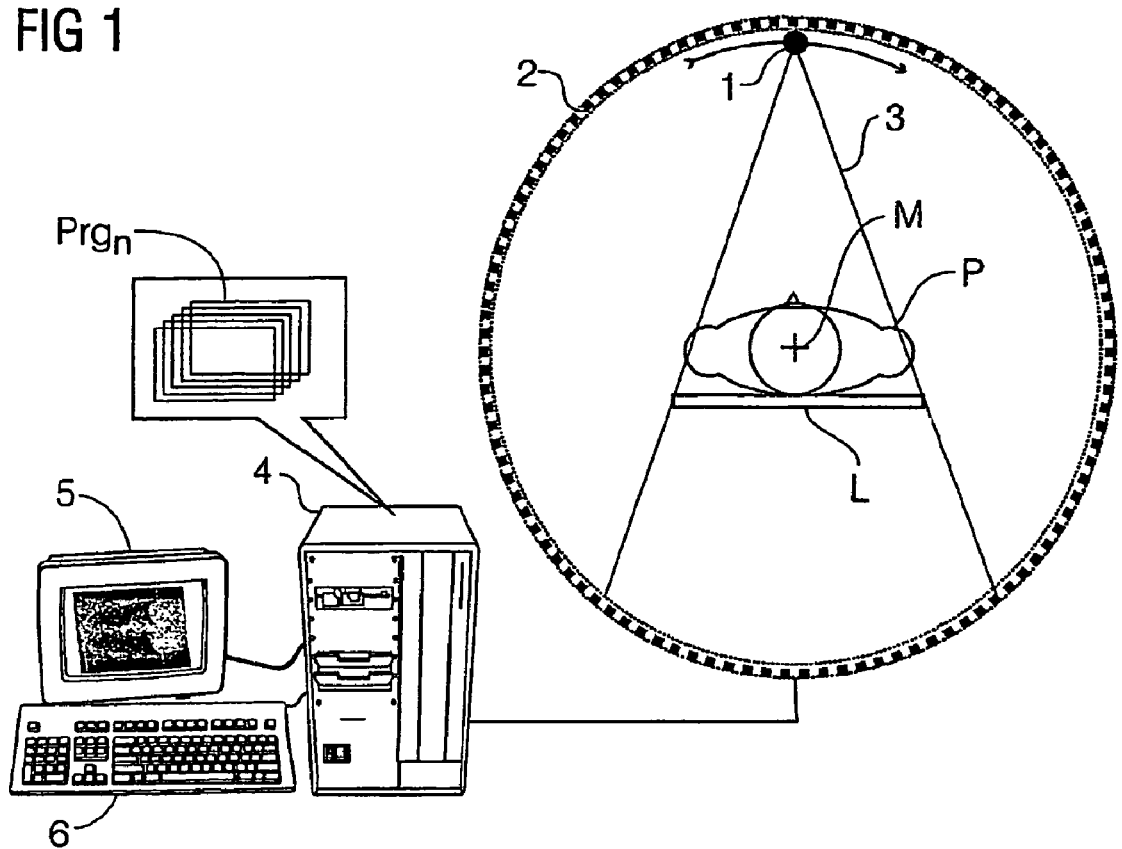
FIG. 1: schematic of a spiral CT.

FIG. 1 shows a schematic of a spiral CT having a focus 1 that rotates about a center point M and emits a conical X-ray beam 3 for scanning a patient P. This conical beam 3 is picked up on the side situated opposite the focus by a multirow detector 2 arranged in the form of a ring over 360°, and measured with reference to its intensity such that it is possible in a way known per se and described many times to display a three-dimensional image of the patient with reference to his/her absorption coefficients. The purpose of evaluating the measured raw data is served by a data processing system 4 that has an output unit 5 and an input unit 6 and in which control and evaluation programs $Prg_n$ run. The basic methods for evaluating the measured raw data are generally known. Reference is made by way of example to the publication already described above at the beginning by Willi A. Kalender, Computertomographie, ISBN 3-89578-082-0. For the rest, a multifarious patent literature is available with reference to these evaluation methods.

Figure 2:
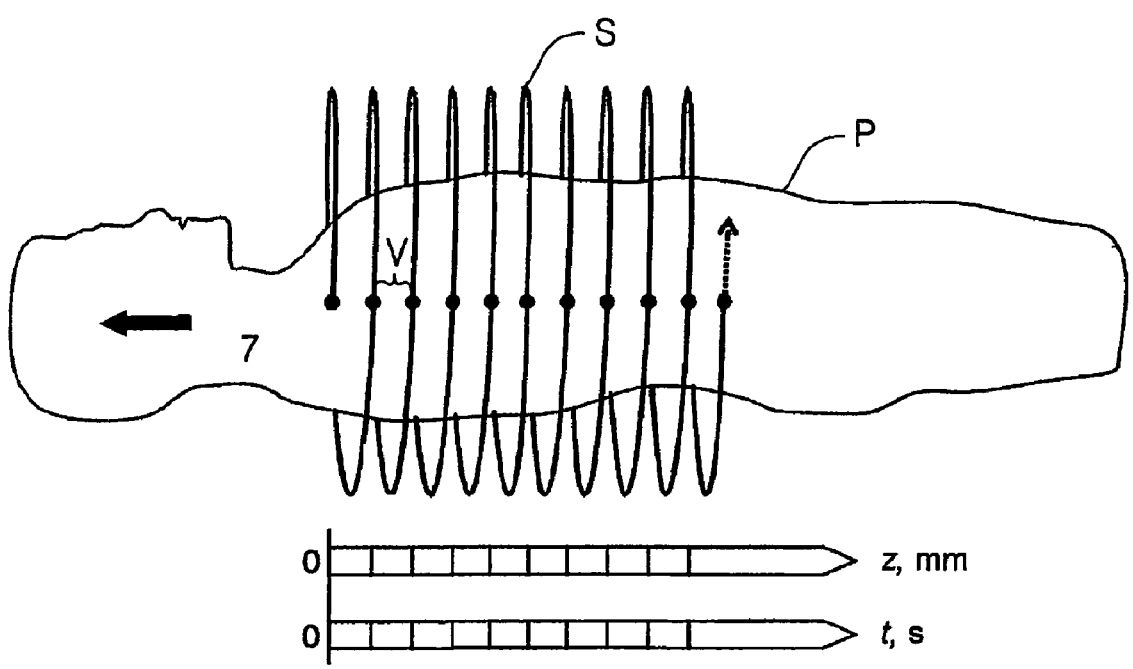
FIG. 2: schematic of a spiral recording.

It is pointed out, furthermore, that embodiments of the present invention do not relate exclusively to the CT illustrated here, but also to single-row or multirow detectors that co-rotate with the focus. They can also be applied with CT units that have a number of foci and a number of detectors. However, it is essential here that the focus be moved relative to the patient on a spiral track, as shown in FIG. 2, when measuring the raw data. This spiral track can be achieved, on the one hand, by feeding the patient in the z-direction while simultaneously rotating the focus on a circular track. On the other hand, it is also possible to fix the patient in space and allow only the focus to rotate about the patient on a spiral track. In this case, either a detector can likewise co-rotate or, given a fixed detector arranged in the form of a circle, said detector can be moved linearly only in the z-direction. The spacing between two spiral points of equal angle is noted in this case by the feed V.

By way of example, in order to carry out the method according to at least one embodiment of the invention a relative movement of the patient in the z-direction is carried out with a CT—as illustrated in FIG. 1—with a non-rotating focus 1 such that it is possible to record a so-called topogram of the patient that corresponds in essence to a transmitted light X-ray picture of the patient perpendicular to the z-direction. However, no X-ray film is exposed here; rather the intensity values of the detectors situated opposite the focus are processed as a function of the distance moved.

Figure 3:
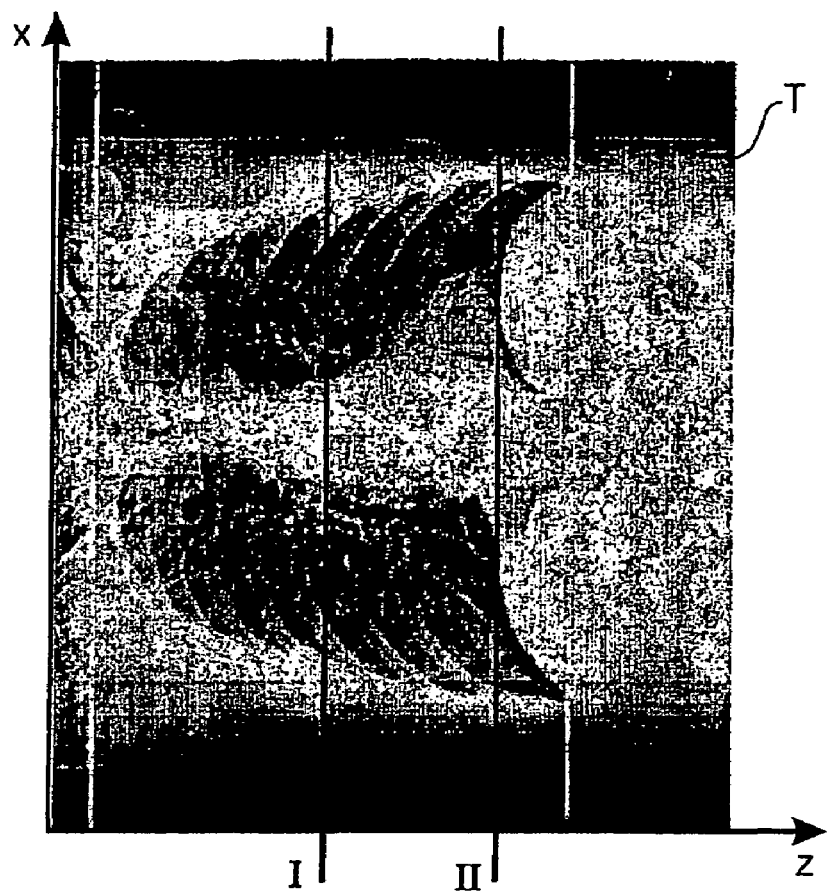
FIG. 3: topogram with boundaries of the moving and stationary zones.

Such a topogram T is illustrated in FIG. 3. It shows the transmitted light picture of the patient P in the thoracic and upper abdominal areas.

This picture can now be used in accordance with the method according to at least one embodiment of the invention to mark manually or, in the fashion supported by an automatic image recognition method, to mark the area of the topogram in which movement fuzziness is to be expected because of the beating heart. Two boundaries I and II are illustrated in the present FIG. 3 for this purpose, the two boundaries I and II respectively marking the upper and lower ends of the heart. Thus, there is marked on the stretch to the left of the boundary line I an area in which no movement or only minimum movement is to be expected, just as in the case in the area to the right of the boundary line II. Because of the beating heart, cyclically occurring movements are to be expected in the area between the boundaries I-II because of the heart beat, rest phases and movement phases corresponding to the cardiac cycles occurring, in turn, in this area I-II over the time axis in a way known per se.

In order to achieve an optimum CT recording, the inventors propose in the particular embodiment outlined here to travel over the entire topogram shown in FIG. 3 with two different feed rates $v_1$ and $v_2$ during a single pass or scan, a normal spiral scan, from which all the measured detector data are used for reconstruction, being covered during the single pass when travelling at the low feed rate, and there being carried out in the section with low feed rate a typical gated spiral reconstruction in which only data from specific cycle areas of the cycle periods of the cyclically moving subareas of the examination object, for example from the rest phases of a heart and/or the neighboring zones and organs, are used for the reconstruction.

Figure 4:
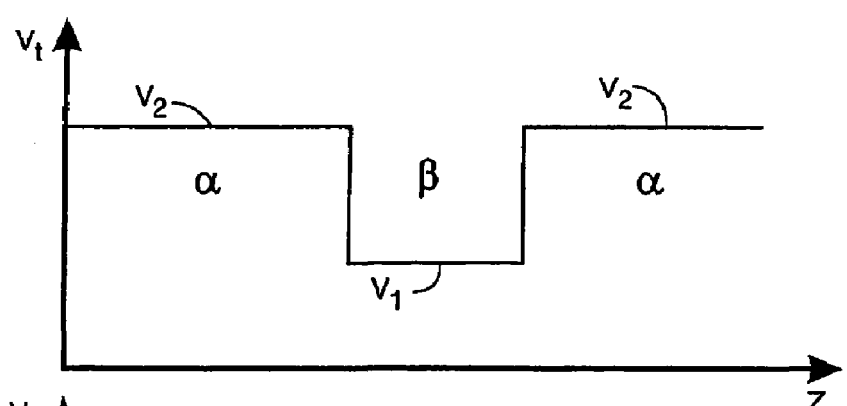
FIG. 4: feed characteristic over the z-axis.

A schematic of these different feed rates over the entire scanning area is illustrated in FIG. 4, which corresponds in its three-dimensional arrangement to the topogram T, situated thereabove, of FIG. 3.

In a first area α, this FIG. 4 shows a high feed rate $v_2$ that is simultaneously coupled to a standard scanning method of a CT, which scanning method corresponds to a spiral scan of a non-moving object in the case of which redundancies that are as slight as possible should occur during measurement.

There follows subsequently between the boundaries I and II an area β in which traveling takes place with a low feed rate $v_1$, a typical cardio evaluation being applied here with reference to the evaluation of the scanned data, care being taken, for example, with the aid of ECG measurements to ensure that use is made for the image evaluation of only beams that are measured during times when the heart is in a rest phase, whereas beams at the time of a movement phase are rejected, or at least given a lesser weight.

At the end of this area β, that is to say following the boundary II, work is done again with a high feed rate, the data collection and image conditioning likewise being performed here again with the aid of a normal scanning method—that is to say without ECG coupling.

If the patient is displaced relative to the gantry on a movable couch, in order to achieve the desired spiral scanning, changing the rate in such a way between two feed rates $v_1$ and $v_2$ can result in an additional movement fuzziness, since the high acceleration during transition between the two rates can lead to an undesired and uncontrolled movement of the patient. This undesired movement, which can likewise result in a fuzziness of recording, can be avoided, or at least diminished, for example, by using a maximum acceleration that avoids such "jumping" of the patient during transition between the two rates. Conversely, it is also possible to avoid an excessively severe mechanical loading of a gantry that can travel in the seating direction with reference to the patient when such a limitation of acceleration is introduced.

Figure 5:
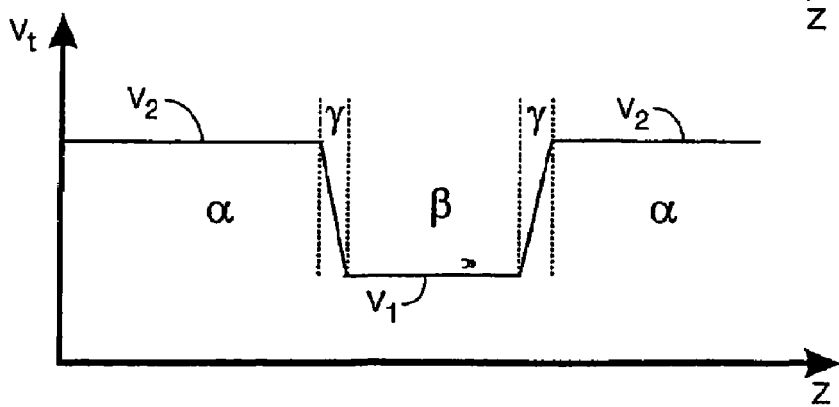
FIG. 5: feed characteristic over the z-axis with restriction of acceleration.

FIG. 5 shows such a method with a maximum acceleration that is to be found in the gradient of the curve of the feed rates, between the feed rates $v_1$ and $v_2$. Here, in addition to the two rate areas α and β an intermediate area γ is introduced in which the transition between the two feed rates $v_1$ and $v_2$ is carried out under controlled positive or negative acceleration.

The inventors propose a further particular embodiment of the method according to at least one embodiment of the invention, doing so on the basis of the fundamental idea of the invention. With this method there is in principle no need to compile a topogram in order to distinguish between moving and stationary scanning areas. However, for the purpose of simplified explanation such a topogram T is illustrated in FIG. 6—the aim being to use it to explain the particular design of the method according to at least one embodiment of the invention.

Figure 6:
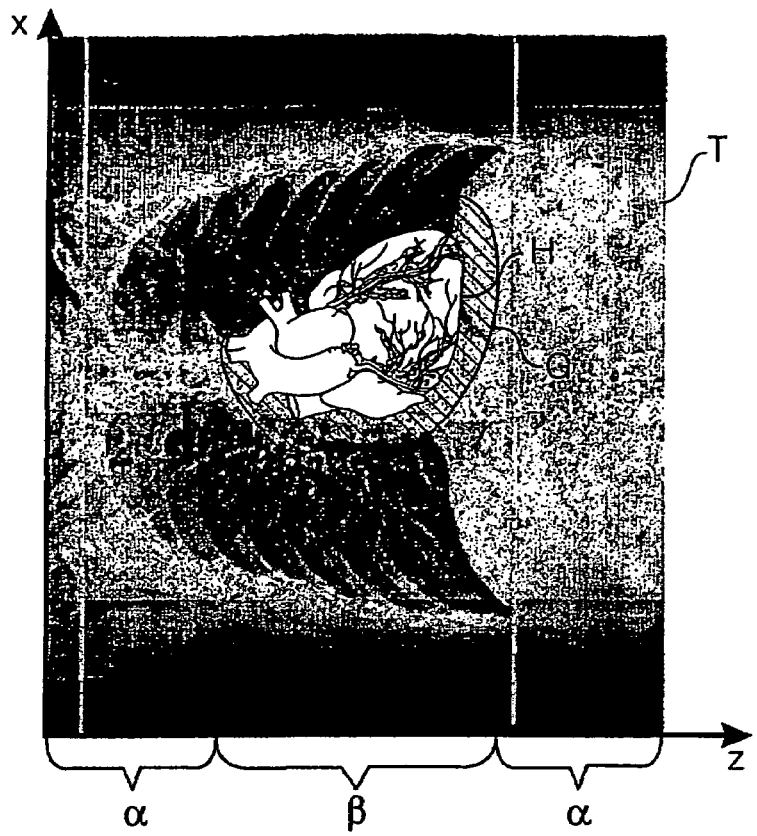
FIG. 6: topogram with moving, stationary and transitional zones.

The topogram from FIG. 6 shows a superposition of a schematically illustrated heart with a hatched boundary area G surrounding this heart. This boundary area G is intended to define the surroundings of the heart that are likewise caused to move because of the heart beats. These surroundings are essentially areas of the lungs and of the diaphragm, together with parts of the adjacent organs. If the patient is now scanned, this scanning begins at a high feed rate, and starting from a 180° rotation of the focus about the patient in conjunction with a conical beam characteristic there are always individual beams present that penetrate the tissue on an identical path, but with a time offset. If the measured absorption values for two time-offset beams with an identical path are compared, it is possible to determine on the basis of the absorption performance whether a movement has taken place in the tissue in the area of these beams, since such a movement leads to a change in the measured intensity as a function of time. It is, for example, possible in this way to detect whether the currently scanned area is being subjected to an instantaneous movement or is in a rest phase.

If this method is carried out when scanning over the z-axis, it is possible while scanning the patient to determine whether moving subareas are located in the current scanning area, and to carry out a corresponding, preferably automatic, change in the scanning rate.

Figure 7:
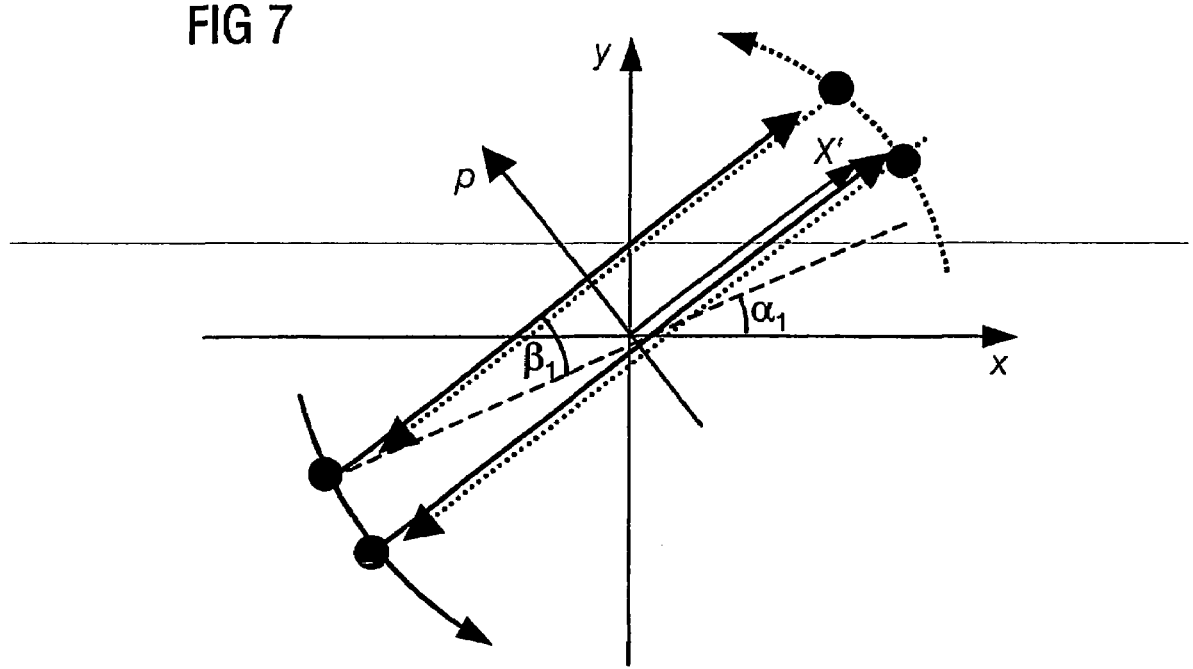
FIG. 7: schematic of the movement detection by means of parallel beams and their complementary returning beams.

Shown further by way of supplement in FIG. 7 is a schematic of the movement detection via parallel beams and their complementary returning beams. A parallel projection onto the local coordinate system with the coordinates x', p, z at the angle $\alpha_1+\beta_1$ is considered here in the global coordinate system with the coordinates x, y, z (z-axis not visible in the 2-dimensional illustration) after the parallel rebinning. $\alpha_1$ corresponds in this case to the angle of rotation in fan geometry, and $\beta_1$ to the angle in the beam fan.

Two oppositely directed beams having solid and dotted lines, respectively, are shown that are measured starting from the focal positions illustrated as a solid point in each case, but with a time offset. If the radiation attenuation determined there remains constant over time, a stationary transradiated object can be assumed, whereas a change in the determined attenuation of beams that are oppositely directed, that is to say offset by 180° and in time, indicates a movement of the scanned object area. Of course, this assumption proceeds from an object with an inhomogeneous mass structure—as is the case with a human and which is to be measured. A detailed description of this method is described in the previously mentioned DE 100 64 785 A1. According to at least one embodiment of the invention, this method can be used both to distinguish a static area from a partially moving area of the examination object, and to trigger a cardio CT reconstruction.

It may be pointed out by way of supplement that ultrasonic information, if appropriate in conjunction with automatic image recognition methods, can also be used to detect the movement or for the automatic distinguishing of moving and stationary areas.

Clearly, the abovementioned features of embodiments of the invention can be used not only in the respectively specified combination, but also in other combinations or on their own without departing from the scope of the invention.

Thus, by way of summary, at least one embodiment of the invention presents a method for producing CT images by use of spiral CT with spiral reconstruction of an examination object moving cyclically in subareas, different feed rates $v_1$ and $v_2$ being used during a scanning pass over the examination object, depending on whether the scanned area is moving cyclically at least partially or is stationary. Likewise presented is a CT that has the steps/devices/apparatuses for carrying out the method described.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for producing CT images of a partially cyclically moving examination object, comprising:
    scanning the examination object in one pass by a spiral movement of at least one focus and at least one detector oppositely situated;
    performing the scanning of the examination region at a relative feed rate between gantry and couch;
    determining a three-dimensional image of absorption coefficients with the aid of a multiplicity of sectional planes of an examination volume on the basis of the data obtained by scanning;
    determining at least one static object area and at least one at least partially moving object area with reference to the examination object with the aid of cyclical intrinsic movement, with a detection of the cyclical intrinsic movement of a subarea of the examination object performed in a current scanning area by comparing an intensity measurement of at least one pair of time-offset rays on a common ray axis, and with the determining performed during the scanning; and using, during a pass when scanning the examination object, a relatively low feed rate upon the determining of the at least one at least partially moving object area, and using a relatively higher feed rate upon the determining of the at least one static object area.

2. The method as claimed in claim 1, wherein a position of a beating heart is determined in order to divide the examination object into the static and moving object areas.

3. The method as claimed in claim 1, wherein the transition between the feed rates is performed with a prescribed maximum acceleration.

4. The method as claimed in claim 1, wherein during scanning at a relatively low feed rate, the movement of the heart is temporally resolved by way of ECG leads and is divided into movement phases and rest phases, with only detected data from the rest phase being used to compile images.

5. The method as claimed in claim 1, wherein scanning uses only detector data from a specific cycle rest phase of the cyclically moving area and uses all the measured detector data of the static area.

6. The method as claimed in claim 1, wherein an intensity of radiation emanating from the at least one focus is matched to a current feed rate.

7. The method as claimed in claim 6, wherein the intensity of radiation is matched by at least one of controlling and regulating a tube current.

8. A CT unit for scanning an at least partially cyclically moving examination object, comprising:
at least one focus from which a beam is emanated;
at least one detector of planar design, including a multiplicity of distributed detector elements for detecting the rays of the beam, the at least one focus being movable relative to the examination object with a feed rate on a spiral focal track revolving about the examination object;
means for determining a three-dimensional image of absorption coefficients with the aid of a multiplicity of sectional planes of an examination volume on the basis of the data obtained by scanning;
means for determining at least one static object area and at least one at least partially moving object area with reference to the examination object with the aid of cyclical intrinsic movement, with a detection of the cyclical intrinsic movement of a subarea of the examination object performed in a current scanning area by comparing an intensity measurement of two oppositely directed rays at two time instants, and with the determining performed during the scanning; and
means for using, during a pass when scanning the examination object, a relatively low feed rate upon the determining of the at least one at least partially moving object area, and using a relatively higher feed rate upon the determining of the at least one static object area.

9. The CT unit as claimed in claim 8, wherein said means are implemented at least partially by at least one of programs and program modules.

10. The CT unit as claimed in claim 9, wherein an apparatus is provided for controlling the feed rate as a function of scanning area.

11. The CT unit as claimed in claim 8, wherein an apparatus is provided for controlling the feed rate as a function of scanning area.

12. A method for producing CT images of a partially cyclically moving examination object, comprising:
scanning the examination object in one pass by a spiral movement of at least one focus and at least one detector oppositely situated;
performing the scanning of the examination region at a relative feed rate between gantry and couch;
determining a three-dimensional image of absorption coefficients with the aid of a multiplicity of sectional planes of an examination volume on the basis of the data obtained by scanning;
determining at least one static object area and at least one at least partially moving object area with reference to the examination object with the aid of cyclical intrinsic movement, with a detection of the cyclical intrinsic movement of a subarea of the examination object performed in a current scanning area by comparing an intensity measurement of at least one pair of time-offset rays on a common ray axis, and with the determining performed during the scanning; and
using, during a pass when scanning the examination object, a first feed rate in the at least one moving object area and using a second feed rate in the at least one static object area.

13. The method as claimed in claim 12, wherein the determination of static and moving object areas before the scan is performed with subsequent manual subdivision of the areas.

14. A CT unit for scanning an at least partially cyclically moving examination object, comprising:
at least one focus from which a beam is emanated;
at least one detector of planar design, including a multiplicity of distributed detector elements for detecting the rays of the beam, the at least one focus being movable relative to the examination object with a feed rate on a spiral focal track revolving about the examination object;
means for determining a three-dimensional image of absorption coefficients with the aid of a multiplicity of sectional planes of an examination volume on the basis of the data obtained by scanning;
means for determining at least one static object area and at least one at least partially moving object area with reference to the examination object with the aid of cyclical intrinsic movement, with a detection of the cyclical intrinsic movement of a subarea of the examination object performed in a current scanning area by comparing an intensity measurement of two oppositely directed rays at two time instants, and with the determining performed during the scanning; and
means for using, during a pass when scanning the examination object, a first feed rate in the at least one at least partially moving object area and a second feed rate in the at least one static object area.

15. The CT unit as claimed in claim 14, wherein the determination of static and moving object areas before the scan is performed with subsequent manual subdivision of the areas.

* * * * *